(12) United States Patent
Joly et al.

(10) Patent No.: US 11,702,602 B2
(45) Date of Patent: Jul. 18, 2023

(54) PRODUCTION OF AROMATICS BY PYROLYSIS, WATER GAS SHIFT AND AROMATIZATION OF CO2

(71) Applicant: IFP Energies Nouvelles, Rueil-Malmaison (FR)

(72) Inventors: Jean-Francois Joly, Rueil-Malmaison (FR); Catherine Laroche, Rueil-Malmaison (FR); Frederic Feugnet, Rueil-Malmaison (FR)

(73) Assignee: IFP Energies Nouvelles, Rueil-Malmaison (FR)

( * ) Notice: Subject to any disclaimer, the term of this patent is extended or adjusted under 35 U.S.C. 154(b) by 0 days.

(21) Appl. No.: 17/487,132

(22) Filed: Sep. 28, 2021

(65) Prior Publication Data
US 2022/0098499 A1 Mar. 31, 2022

(30) Foreign Application Priority Data
Sep. 29, 2020 (FR) ...................................... 2009872

(51) Int. Cl.
*C10G 61/02* (2006.01)
*B01D 3/14* (2006.01)
*B01D 11/04* (2006.01)
*B01J 19/24* (2006.01)
*C10G 2/00* (2006.01)
(Continued)

(52) U.S. Cl.
CPC ............ *C10G 61/02* (2013.01); *B01D 3/143* (2013.01); *B01D 11/0488* (2013.01); *B01D 11/0492* (2013.01); *B01J 19/245* (2013.01); *C10G 2/50* (2013.01); *C10G 63/02* (2013.01); *C10G 69/02* (2013.01); *C10K 3/04* (2013.01); *B01J 2219/0004* (2013.01); *C10G 2300/4006* (2013.01); *C10G 2300/4012* (2013.01); *C10G 2300/4018* (2013.01); *C10G 2400/30* (2013.01)

(58) Field of Classification Search
CPC .......... C10G 61/02; C10G 2/50; C10G 63/02; C10G 69/02; C10G 2300/4006; C10G 2300/4012; C10G 2300/4018; C10G 2400/30; B01D 3/143; B01D 11/0488; B01D 11/0492; B01D 19/245; C10K 3/04
See application file for complete search history.

(56) References Cited

U.S. PATENT DOCUMENTS

| 2016/0304788 A1 | 10/2016 | Sorensen et al. |
| 2017/0362143 A1 | 12/2017 | Bilaus et al. |

OTHER PUBLICATIONS

French Search Report dated Jun. 9, 2021 issued in corresponding FR 2009872 application (2 pages).

*Primary Examiner* — Jafar F Parsa
(74) *Attorney, Agent, or Firm* — Millen White Zelano and Branigan, PC; Csaba Henter

(57) ABSTRACT

Device and process for converting a feedstock of aromatic compounds, in which the feedstock is notably treated using a fractionation train (4-7), a xylenes separating unit (10) and an isomerization unit (11), and in which a pyrolysis unit (13) treats a second hydrocarbon-based feedstock, produces a pyrolysis effluent feeding the feedstock, and produces a pyrolysis gas comprising CO, CO2 and H2; a WGS water gas shift reaction section (50) suitable for treating the pyrolysis gas and for producing a WGS gas enriched in CO2 and in hydrogen; a CO2 aromatization reaction section (52) suitable for: at least partly treating the WGS gas to produce a hydrocarbon effluent comprising aromatic compounds, and feeding the feedstock with the hydrocarbon effluent.

19 Claims, 1 Drawing Sheet

(51) Int. Cl.
*C10G 63/02* (2006.01)
*C10G 69/02* (2006.01)
*C10K 3/04* (2006.01)

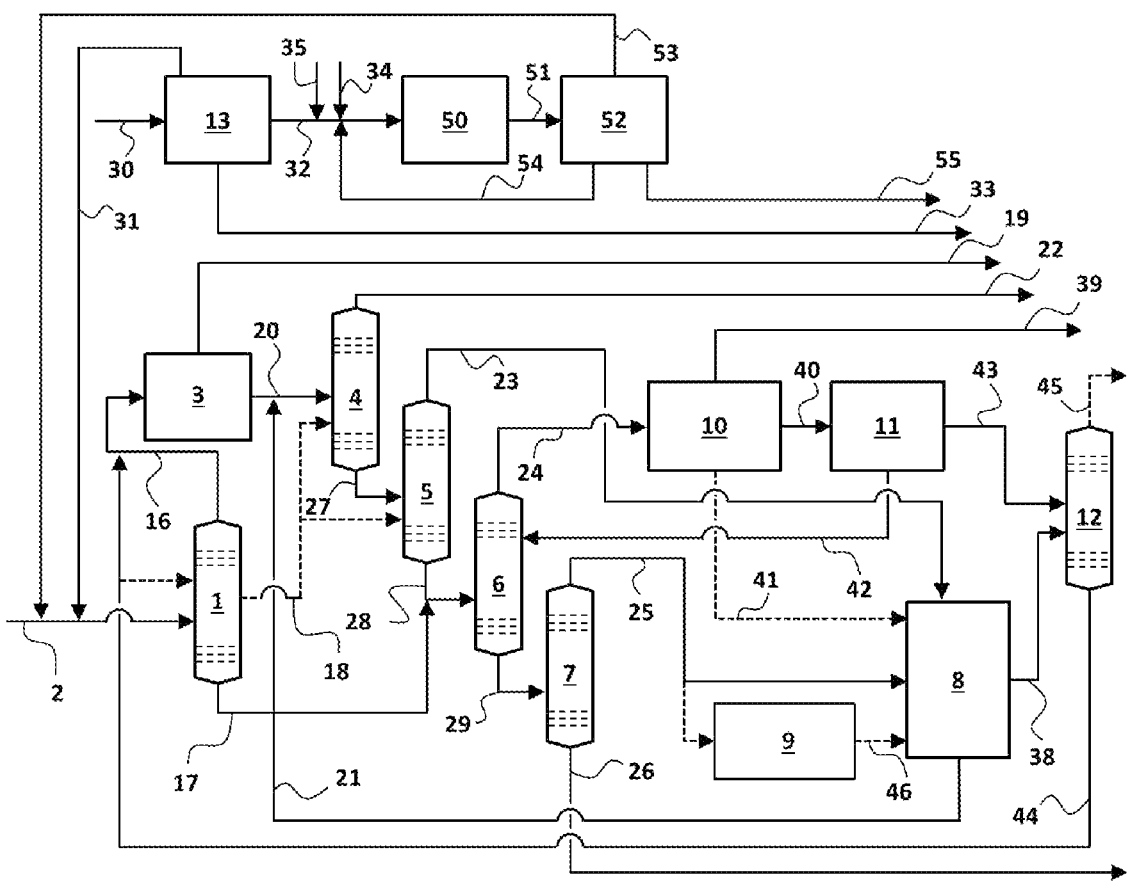

PRODUCTION OF AROMATICS BY PYROLYSIS, WATER GAS SHIFT AND AROMATIZATION OF CO2

TECHNICAL FIELD

The invention relates to the production of aromatics for the petrochemical industry (benzene, toluene and xylenes, i.e. BTX). More particularly, the object of the invention is to be able to increase the production of aromatics, and notably of para-xylene, produced by a process of pyrolysis of hydrocarbon-based compounds, and preferably of biomass, by conversion of CO and CO2 which are byproducts of the pyrolysis, the total amount of the carbon and in particular of the biobased carbon thus being able to be upgraded.

An aromatic complex (or device for the conversion of aromatic compounds) is a device fed with feedstocks predominantly composed of six to ten carbon atoms or more, referred to as C6 to C10+ feedstocks. Various sources of aromatic compounds may be introduced into an aromatic complex, the most widespread being obtained from a process for the catalytic reforming of naphtha.

Within an aromatic complex, whatever the source of aromatics, benzene and alkylaromatics (e.g. toluene, para-xylene, ortho-xylene) are extracted therefrom and are then converted into desired intermediates. The products of interest are aromatics with 0 (benzene), 1 (toluene) or 2 (xylenes) methyl groups, and in particular, among the xylenes, para-xylene, having the greatest market value.

Processes for the pyrolysis of hydrocarbon-based compounds produce aromatic compounds, but also a lot of CO and CO2 as conversion byproducts. When the pyrolysis is catalytic, combustion of the coke present on the catalyst used in the pyrolysis reactor also produces an appreciable amount of CO2.

PRIOR ART

To date, aromatic complexes make it possible to produce benzene, optionally toluene, and xylenes (often para-xylene, sometimes ortho-xylene). An aromatic complex generally has at least one catalytic unit having at least one of the following functions:
- the isomerization of aromatic compounds containing eight carbon atoms, denoted A8 compounds, making it possible to convert ortho-xylene, meta-xylene and ethylbenzene into para-xylene;
- transalkylation, making it possible to produce xylenes from a mixture of toluene (and optionally of benzene) and of A9+ compounds, such as trimethylbenzenes and tetramethylbenzenes; and
- the disproportionation of toluene, which makes it possible to produce benzene and xylenes.

The aromatic loop makes it possible to produce high-purity para-xylene by separation by adsorption or by crystallization, an operation which is well known from the prior art. This "08-aromatic loop" includes a step of removal of the heavy compounds (i.e., C9+ compounds) in a distillation column known as a "xylenes column". The top stream from this column, which contains the C8− aromatic isomers (i.e. A8 isomers), is subsequently sent to the process for separation of the para-xylene which is, very generally, a process for separation by simulated moving bed (SMB) adsorption, to produce an extract and a raffinate, or a crystallization process, in which a para-xylene fraction is isolated from the remainder of the constituents of the mixture in the form of crystals.

The extract, which contains the para-xylene, is subsequently distilled in order to obtain high-purity para-xylene. The raffinate, which is rich in meta-xylene, ortho-xylene and ethylbenzene, is treated in a catalytic isomerization unit which restores a mixture of C8 aromatics in which the proportion of the xylenes (ortho-, meta-, para-xylenes) is virtually at thermodynamic equilibrium and the amount of ethylbenzene is reduced. This mixture is again sent to the "xylenes column" with the fresh feedstock.

Aromatic complexes producing benzene and para-xylene are very predominantly fed with feedstocks obtained from petroleum or natural gas. These complexes do not make it possible to produce biobased aromatics. Another challenge is that of upgrading carbon in the form of CO and CO2, and in particular biobased carbon, into compounds with high added value. The object of the present invention is to overcome these drawbacks.

SUMMARY OF THE INVENTION

In the context described previously, a first object of the present description is to overcome the problems of the prior art and to provide a device and a process for the production of aromatics for the petrochemical industry making it possible, when the aromatic compounds are produced by pyrolysis of hydrocarbon-based compounds, to convert (for example all of) the CO and CO2, byproducts of the pyrolysis section, into additional paraffins and aromatic compounds. The CO2 originating from the combustion of the coke present on the pyrolysis process catalyst may also be advantageously converted into aromatic compounds.

The invention is based on the conversion of carbon monoxide, i.e. CO, and of carbon dioxide, i.e. CO2, into paraffins and aromatic compounds which are introduced into the aromatic complex, and notably on the provision of one or more units for converting CO into CO2 (and into hydrogen), and for converting the CO2 into aromatic compounds in one step in a dedicated aromatization reactor. The aromatic compounds obtained from the conversion of CO2 are treated in the aromatic loop as a mixture with the aromatic compounds obtained directly from the pyrolysis of the hydrocarbon-based compounds.

Specifically, the object of the present invention may be resumed as adding a water gas shift (or WGS) unit to at least partially convert CO into CO2 and thus to obtain a CO2-enriched gas, followed by a unit for aromatization of the CO2. At the outlet of the CO2 aromatization unit, the CO produced and the unconverted CO2 are recycled to the inlet of the WGS unit. The conversion of the CO and CO2 may then be complete. The aromatic compounds obtained from the aromatization of CO2 are introduced into the aromatic loop to be transformed therein into benzene and para-xylene.

According to a first aspect, the abovementioned objects, and also other advantages, are obtained by a device for converting a first hydrocarbon-based feedstock comprising aromatic compounds, comprising:
- a fractionation train suitable for extracting at least one cut comprising benzene, one cut comprising toluene and one cut comprising xylenes and ethylbenzene from the first hydrocarbon-based feedstock;
- a unit for the separation of the xylenes suitable for treating the cut comprising xylenes and ethylbenzene and for producing an extract comprising para-xylene and a raffinate comprising ortho-xylene, meta-xylene and ethylbenzene;

an isomerization unit suitable for treating the raffinate and for producing an isomerate enriched in para-xylene which is sent to the fractionation train;

a pyrolysis unit suitable for treating a second hydrocarbon-based feedstock, for producing at least one pyrolysis effluent comprising hydrocarbon-based compounds of 6 to 10 carbon atoms at least partially feeding the first hydrocarbon-based feedstock, and for producing a pyrolysis gas comprising at least CO, CO2 and H2;

a WGS water gas shift reaction section suitable for treating the pyrolysis gas and for producing a WGS gas enriched in CO2 and in hydrogen;

a CO2 aromatization reaction section suitable for:
  at least partly treating the WGS gas to produce a hydrocarbon effluent comprising aromatic compounds, and
  feeding the first hydrocarbon-based feedstock with the hydrocarbon effluent.

One of the advantages of the invention is notably that of being able to convert CO2 into aromatic compounds in a single step and of being able, by means of recycling, to convert all of the CO2 and CO.

According to one or more embodiments, the device also comprises a recycling line suitable for recycling, to the inlet of the WGS reaction section, the unconverted CO2 and also the CO and water formed during the aromatization reaction.

According to one or more embodiments, the device also comprises at least one supply line to provide a supply of H2O and/or hydrogen in the pyrolysis gas, upstream of the WGS section.

According to one or more embodiments, the fractionation train is suitable for extracting a C9-C10 monoaromatics cut from the first hydrocarbon-based feedstock.

According to one or more embodiments, the device also comprises a transalkylation unit suitable for treating the C9-C10 monoaromatics cut with the cut comprising toluene and for producing xylenes which are sent to the fractionation train.

According to one or more embodiments, the device also comprises a selective hydrogenolysis unit is suitable for:
  treating the C9-C10 monoaromatics cut; and
  producing a hydrogenolysis effluent enriched in methyl-substituted aromatic compounds which is sent to the transalkylation unit.

According to one or more embodiments, the device also comprises a disproportionating unit suitable for at least partly treating the cut comprising toluene and for producing a xylene-enriched cut, which is recycled to the isomerization unit.

According to a second aspect, the abovementioned objects, and also other advantages, are obtained by a process for converting a first hydrocarbon-based feedstock comprising aromatic compounds, comprising the following steps:
  fractionating the first hydrocarbon-based feedstock in a fractionation train to extract at least one cut comprising benzene, one cut comprising toluene and one cut comprising xylenes and ethylbenzene;
  separating the cut comprising xylenes and ethylbenzene in a xylenes separating unit and producing an extract comprising para-xylene and a raffinate comprising ortho-xylene, meta-xylene and ethylbenzene;
  isomerizing the raffinate in an isomerization unit and producing an isomerate enriched in para-xylene;
  sending the isomerate enriched in para-xylene to the fractionation train;
  treating a second hydrocarbon-based feedstock in a pyrolysis unit to produce at least one pyrolysis effluent comprising hydrocarbon-based compounds containing from 6 to 10 carbon atoms feeding, at least partially, the first hydrocarbon-based feedstock and to produce a pyrolysis gas comprising at least CO, CO2 and H2;
  treating the pyrolysis gas in a WGS water gas shift reaction section to produce a WGS gas enriched in CO2 and in hydrogen;
  at least partly treating the WGS gas enriched in CO2 and in hydrogen in an aromatization reaction section to produce a hydrocarbon effluent comprising aromatic compounds; and
  feeding the first hydrocarbon-based feedstock with the hydrocarbon effluent.

According to one or more embodiments, the process involves recycling, to the inlet of the WGS reaction section, the unconverted CO2 and also the CO and water formed during the aromatization reaction.

According to one or more embodiments, the process also involves providing a supply of H2 and/or H2O in the pyrolysis gas by means of at least one supply line.

According to one or more embodiments, the pyrolysis unit comprises at least one reactor used under at least one of the following operating conditions:
  absolute pressure of between 0.1 and 0.5 MPa and HSV of between 0.01 and 10 $h^{-1}$, preferably between 0.01 and 5 $h^{-1}$ and very preferably between 0.1 and 3 $h^{-1}$, the HSV being the ratio of the flow rate by volume of feedstock to the volume of catalyst used;
  temperature of between 400° C. and 1000° C., preferably between 400° C. and 650° C., preferably between 450° C. and 600° C. and preferably between 450° C. and 590° C.;
  zeolite catalyst comprising and preferably consisting of at least one zeolite chosen from ZSM-5, ferrierite, zeolite beta, zeolite Y, mordenite, ZSM-23, ZSM-57, EU-1 and ZSM-11, and preferably the catalyst is a catalyst comprising only ZSM-5.

According to one or more embodiments, the WGS reaction section comprises at least one reactor used under at least one of the following operating conditions:
  temperature of between 250° C. and 450° C., preferentially between 300° C. and 500° C. and even more preferentially between 310° C. and 450° C.;
  pressure of between 0.1 and 5 MPa, preferentially between 0.2 and 4 MPa and more preferentially between 0.5 and 3 MPa;
  an H2O/CO mole ratio of between 1 and 4, preferably between 1.5 and 2.5, very preferably between 1.8 and 2.2, such as 2 (±0.1);
  space velocity of the gas entering the reactor of between 1000 and 30 000 $mL/g_{cata}/h$.

According to one or more embodiments, the reaction section for the aromatization of the CO2 comprises at least one reactor used under at least one of the following operating conditions:
  temperature of between 280° C. and 350° C., preferentially between 300° C. and 400° C. and even more preferentially between 320° C. and 380° C.;
  pressure of between 0.1 and 10 MPa, preferentially between 0.5 and 8 MPa and more preferentially between 2 and 4 MPa;
  space velocity of the gas entering the reactor of between 500 and 3000 $mL/g_{cata}/h$.

According to one or more embodiments, the isomerization unit comprises a gas-phase isomerization zone and/or a liquid-phase isomerization zone, in which the gas-phase isomerization zone is used under at least one of the following operating conditions:
temperature of greater than 300° C.;
pressure of less than 4.0 MPa;
hourly space velocity of less than 10 h$^{-1}$;
hydrogen to hydrocarbon mole ratio of less than 10;
in the presence of a catalyst including at least one zeolite having channels, the opening of which is defined by a ring containing 10 or 12 oxygen atoms, and at least one group VIII metal in a content of between 0.1% and 0.3% by weight, limits included, and in which the liquid-phase isomerization zone is used under at least one of the following operating conditions:
temperature of less than 300° C.;
pressure of less than 4 MPa;
hourly space velocity of less than 10 h$^{-1}$;
in the presence of a catalyst including at least one zeolite having channels, the opening of which is defined by a ring containing 10 or 12 oxygen atoms.

Embodiments according to the first aspect and the second aspect, and also other characteristics and advantages of the devices and processes according to the abovementioned aspects, will become apparent on reading the description which follows, which is given solely by way of illustration and without limitation, and with reference to the following drawing.

LIST OF FIGURES

FIG. 1 represents a diagrammatic view of a process according to the present invention for increasing the production of aromatic compounds.

DESCRIPTION OF THE EMBODIMENTS

Embodiments of the device according to the first aspect and of the process according to the second aspect will now be described in detail. In the detailed description that follows, numerous specific details are set out in order to convey a deeper understanding of the device. However, it will be apparent to a person skilled in the art that the device can be implemented without these specific details. In other cases, well-known characteristics have not been described in detail in order to avoid unnecessarily complicating the description.

In the present patent application, the term "to comprise" is synonymous with (means the same thing as) "to include" and "to contain", and is inclusive or open and does not exclude other elements which are not stated. It is understood that the term "to comprise" includes the exclusive and closed term "to consist". In addition, in the present description, an effluent essentially or solely comprising compounds A corresponds to an effluent comprising at least 80% or 90% by weight, preferably at least 95% by weight, very preferably at least 99% by weight, of compounds A.

The present invention may be defined as a device and a process comprising a sequence of unitary operations for producing para-xylene and benzene.

The device and the process according to the invention are characterized in that they comprise and use the catalytic units and the separation units which are known to a person skilled in the art for producing benzene and para-xylene, which units are commonly encountered in aromatic complexes.

One of the characteristics of the present invention may be resumed as the use of CO and CO2, which are byproducts of a unit for the pyrolysis of hydrocarbon-based compounds, for increasing the production of aromatic compounds.

Advantageously, the combination of a reaction section for the conversion of CO into CO2 by WGS reaction, of a reaction section for the aromatization of the CO2, and of introduction of the aromatic compounds obtained from the CO2 aromatization section into the aromatic loop makes it possible to notably increase the amount of aromatics produced by pyrolysis of hydrocarbon-based compounds and to potentially upgrade all of the CO and CO2 which are byproducts of the pyrolysis unit.

With reference to FIG. 1, according to one or more embodiments, the device for conversion of aromatic compounds comprises:
an optional feedstock separation unit 1 for separating the first hydrocarbon-based feedstock 2 of the aromatic complex into a hydrocarbon cut containing 7 or less carbon atoms (C7−) and an aromatic cut containing 8 or more carbon atoms (A8+);
an optional unit for extraction of the aromatics 3 between the feedstock separation unit 1 and a fractionation train 4-7 in order to separate the aliphatic compounds from the benzene and the toluene of the C7− cut of the feedstock of the complex;
the fractionation train 4-7 downstream of the optional unit for extraction of the aromatics 3 making it possible to extract the benzene, the toluene and the xylenes from the other aromatics;
an optional transalkylation unit 8 which converts toluene (and optionally benzene) and methylalkylbenzenes, such as trimethylbenzenes, into xylenes—advantageously, this unit can also treat tetramethylbenzenes;
an optional selective hydrogenolysis unit 9 suitable for treating a cut comprising aromatic compounds containing 9 and 10 carbon atoms and for producing a hydrogenolysis effluent enriched in methyl-substituted aromatic compounds;
an optional separation unit (not shown) for separating the hydrogenolysis effluent located (e.g. directly) downstream of the selective hydrogenolysis unit 9, for producing a plurality of liquid effluent cuts;
a unit for the separation of the xylenes 10 (e.g. of the crystallization or simulated moving bed type using a molecular sieve and a desorbent, such as toluene) making it possible to isolate the para-xylene from the xylenes and the ethylbenzene;
a unit for isomerization 11 of the raffinate obtained as effluent from the unit for the separation of the xylenes 10, in order notably to convert the ortho-xylene, the meta-xylene and the ethylbenzene into para-xylene;
an optional stabilization column 12 which makes it possible notably to remove the more volatile species (e.g. C5− species) from the aromatic complex, notably effluents from the transalkylation unit 8 and/or the isomerization unit 11;
a pyrolysis unit 13, preferably a catalytic pyrolysis unit, for treating a second hydrocarbon-based feedstock 30, producing a pyrolysis effluent 31 at least partially feeding the first hydrocarbon-based feedstock 2 of the aromatic complex, a pyrolysis gas 32 comprising CO, CO2 and H2, and byproducts 33 (mainly composed of middle distillates which, after hydrotreating and/or hydrocracking, can be upgraded in the form of jet fuel, gas oil or marine fuel oil);
a first optional supply line 34 for providing a supply of H2 in the pyrolysis gas 32;

a second optional supply line 35 for providing a supply of H2O at the inlet of the WGS reaction section;

a WGS reaction section 50 for treating the pyrolysis gas 32 coming from the pyrolysis unit 13, and for producing a WGS gas 51 enriched in CO2 and in hydrogen (and thus depleted in CO and in H2O) relative to the pyrolysis gas 32;

a CO2 aromatization reaction section 52 for treating the WGS gas 51 enriched in CO2 and producing a hydrocarbon effluent 53 enriched in aromatic compounds relative to the WGS gas 51;

an optional line 54 for recycling the unconverted CO2, and the CO and H2O formed in the aromatization reaction section 52 to the inlet of the WGS reaction section 50;

an optional outlet line 55 for extracting the water at the outlet of the aromatization reaction section 52;

a feed line 53 for introducing the hydrocarbon effluent 53 of the aromatization section 52 to the inlet of the fractionation zone 1, by feeding the first hydrocarbon-based feedstock 2.

With reference to FIG. 1, the feedstock separating unit 1 treats the first hydrocarbon-based feedstock 2 of the aromatic complex in order to separate a top cut 16 comprising (e.g. essentially) compounds containing 7 or less carbon atoms (C7−), notably containing benzene and toluene, and a bottom cut 17 comprising (e.g. essentially) aromatics containing 8 or more carbon atoms (A8+) which is sent to the xylene column 6. According to one or more embodiments, the feedstock separating unit 1 also separates a first toluene cut 18 comprising at least 90% by weight, preferably at least 95% by weight, very preferably at least 99% by weight of toluene. According to one or more embodiments, the first toluene cut 18 is sent to the first column for the distillation of aromatic compounds 4, also referred to as the benzene column, and/or to the second column for the distillation of aromatic compounds 5, also referred to as the toluene column.

According to one or more embodiments, the first hydrocarbon-based feedstock 2 is a hydrocarbon cut predominantly containing (i.e. >50% by weight) molecules whose carbon number ranges from 6 to 10 carbon atoms. This feedstock may also contain molecules containing more than 10 carbon atoms and/or molecules containing 5 carbon atoms.

The first hydrocarbon-based feedstock 2 of the aromatic complex is rich in aromatics (e.g. >50% by weight) and contains preferably at least 20% by weight of benzene, preferentially at least 30% by weight, very preferably at least 40% by weight of benzene. The first hydrocarbon-based feedstock 2 may be produced by catalytic reforming of a naphtha or may be a product of a cracking (e.g. steam cracking, catalytic cracking) unit or any other means for producing alkylaromatics.

According to one or more embodiments, the first hydrocarbon-based feedstock 2 is at least partially or even totally biobased. According to one or more embodiments, the first hydrocarbon-based feedstock 2 originates (essentially) from a lignocellulosic biomass conversion process. For example, an effluent produced by conversion of lignocellulosic biomass may be treated to meet the specifications required for the first hydrocarbon-based feedstock 2 so as to have contents of sulfur, nitrogen and oxygen elements that are compatible with an aromatic complex.

According to one or more embodiments, the first hydrocarbon-based feedstock 2 of the aromatic complex comprises at least 25% by weight, preferably at least 30% by weight, very preferably at least 35% by weight, of pyrolysis effluent 31 originating from the pyrolysis unit 13 relative to the total weight of the feedstock, the remainder comprising (preferably consisting of) the hydrocarbon effluent 53. According to one or more embodiments, the first hydrocarbon-based feedstock 2 may comprise a mixture of biobased aromatic and paraffinic compounds and a mixture of non-biobased aromatic and paraffinic compounds (for example originating from a catalytic reforming unit).

According to one or more embodiments, the first hydrocarbon-based feedstock 2 comprises less than 10 ppm by weight, preferably less than 5 ppm by weight, very preferably less than 1 ppm by weight, of elemental nitrogen, and/or less than 10 ppm by weight, preferably less than 5 ppm by weight, very preferably less than 1 ppm by weight, of elemental sulfur, and/or less than 100 ppm by weight, preferably less than 50 ppm by weight, very preferably less than 10 ppm by weight, of elemental oxygen.

The top cut 16 from the feedstock separation unit 1, optionally mixed with the bottom product (benzene and toluene) from the stabilization column 12, which will be defined below, is sent to the unit for extraction of the aromatics 3 in order to extract an effluent 19 comprising C6-C7 aliphatic species, which is exported as co-product from the aromatic complex. The aromatic cut 20 (essentially benzene and toluene), referred to as the extract from the unit for extraction of the aromatics 3, optionally mixed with the heavy fraction 21 from the transalkylation unit 8, which will be defined below, is sent to the benzene column 4. According to one or more embodiments, the aromatic cut 20 is a C6-C7 (e.g. essentially) aromatic hydrocarbon-based feedstock (A6-A7).

According to one or more embodiments, the fractionation train comprises the columns for the distillation of aromatic compounds 4, 5, 6 and 7, making it possible to separate the following five cuts:

a cut comprising (e.g. essentially) benzene 22;

a cut comprising (e.g. essentially) toluene 23;

a cut comprising (e.g. essentially) xylenes and ethylbenzene 24;

a cut comprising (e.g. essentially) aromatic compounds containing 9 and 10 carbon atoms 25;

a cut comprising (e.g. essentially) aromatic compounds, the most volatile species of which are aromatics containing 10 carbon atoms 26.

The benzene column 4 is suitable for: treating the aromatic cut 20, which is a C6-C10 (e.g. essentially) aromatic hydrocarbon-based feedstock (A6+); producing, at the top, the cut comprising benzene 22, which may be one of the desired products at the outlet of the aromatic complex; and producing, at the bottom, a C7-C10 (e.g. essentially) aromatic effluent 27 (A7+).

The toluene column 5 is suitable for: treating the C7-C10 aromatic effluent 27 (A7+), which is the bottom product from the benzene column 4; producing, at the top, the cut comprising toluene 23, which is sent to the transalkylation unit 8; and producing, at the bottom, a C8-C10 (e.g. essentially) aromatic effluent 28 (A8+).

The third column for the distillation of aromatic compounds 6, also referred to as the xylene column, is suitable for: treating the aromatic cut containing 8 or more carbon atoms 17 (A8+) of the feedstock of the aromatic complex and optionally the bottom effluent from the toluene column 28; producing, at the top, the cut comprising xylenes and ethylbenzene 24, which is sent to the unit for the separation of the xylenes 10; and producing, at the bottom, an effluent (e.g. essentially) comprising C9-C10 aromatics 29 (A9+).

The fourth column for the distillation of aromatic compounds 7, also referred to as the heavy aromatics column, is optional and is suitable for: treating the bottom effluent from the xylene column 29; producing, at the top, the fraction comprising C9-C10 monoaromatics 25; and producing, at the bottom, the cut comprising (e.g. essentially) aromatic compounds, the most volatile species of which are aromatics containing 10 carbon atoms 26 (A10+). Preferably, the bottom cut 26 comprises C11+ compounds.

In the transalkylation unit 8, the fraction comprising C9-C10 monoaromatics 25 (and/or the hydrogenolysis effluent enriched in methyl-substituted aromatic compounds described below) is mixed with the cut comprising toluene 23 originating from the top of the toluene column 5 and feeds the reaction section of the transalkylation unit 8 to produce xylenes by transalkylation of aromatics with a deficit of methyl groups (toluene) and aromatics with an excess of methyl groups (e.g. tri- and tetramethylbenzenes). According to one or more embodiments, the transalkylation unit 8 is fed with benzene (line not represented in FIG. 1), for example when an excess of methyl groups is observed, for the production of para-xylene. According to one or more embodiments, the transalkylation unit 8 directly treats the bottom effluent from the xylene column 29.

According to one or more embodiments, the transalkylation unit 8 comprises at least one first transalkylation reactor suitable for use under at least one of the following operating conditions:
- temperature of between 200° C. and 600° C., preferentially between 350° C. and 550° C. and even more preferentially between 380° C. and 500° C.;
- pressure of between 2 and 10 MPa, preferentially between 2 and 6 MPa and more preferentially between 2 and 4 MPa;
- WHSV of between 0.5 and 5 $h^{-1}$, preferentially between 1 and 4 $h^{-1}$, and more preferentially between 2 and 3 $h^{-1}$.

According to one or more embodiments, the first transalkylation reactor is operated in the presence of a catalyst comprising zeolite, for example ZSM-5. According to one or more embodiments, the second transalkylation reactor is of fixed bed type.

According to one or more embodiments, the effluents from the reaction section of the transalkylation unit 8 are separated in a first separation column (not represented) downstream of said reaction section of the transalkylation unit 8. A cut comprising at least a part of the benzene, and the more volatile species, 38 (C6−) is extracted at the top of the first separation column and is sent to an optional stabilization column 12, making it possible notably to remove the more volatile species (e.g. C5−) from the aromatic complex. The heavy fraction 21 of the effluents from the first separation column comprising (e.g. essentially) aromatics containing at least 7 carbon atoms (A7+) is optionally recycled to the fractionation train 4-7, for example to the benzene column 4.

The cut comprising xylenes and ethylbenzene 24 is treated in the unit for the separation of the xylenes 10 to produce a fraction or an extract 39, comprising para-xylene, and a raffinate 40. The extract 39 can be subsequently distilled (e.g. if separation by adsorption SMB), for example by means of an extract column and then of an additional toluene column (which are not shown) in the case where toluene is used as desorbent, in order to obtain high-purity para-xylene exported as main product. The raffinate 40 from the unit for the separation of the xylenes 10 comprises (e.g. essentially) ortho-xylene, meta-xylene and ethylbenzene and feeds the isomerization unit 11.

According to one or more embodiments, the xylenes separating unit 10 also separates a second toluene cut 41 comprising at least 90% by weight, preferably at least 95% by weight and very preferably at least 99% by weight of toluene. The toluene cut 41 may be, for example, a part of the toluene used as desorbent when the unit for the separation of the xylenes 10 comprises a "simulated moving bed" adsorption unit. According to one or more embodiments, the second toluene cut 41 is sent to the transalkylation unit 8.

In the isomerization reaction section of the isomerization unit 11, the para-xylene isomers are isomerized, whereas the ethylbenzene can be: isomerized to give a mixture of C8 aromatics, for example if it is desired to produce mainly para-xylene; and/or dealkylated to produce benzene, for example if it is desired to produce both para-xylene and benzene. According to one or more embodiments, the effluents from the isomerization reaction section are sent to a second separation column (not represented) to produce, at the bottom, an isomerate 42 enriched in para-xylene, which is preferably recycled to the xylene column 6; and to produce, at the top, a hydrocarbon cut comprising compounds containing 7 or less carbon atoms 43 (C7−) which is sent to the optional stabilization column 12, for example with the cut comprising at least a part of the benzene, and the more volatile species, 38.

According to one or more embodiments, the isomerization unit 11 comprises a first isomerization zone working in the liquid phase and/or a second isomerization zone working in the gas phase, as is described in the patents listed above. According to one or more embodiments, the isomerization unit 11 comprises a first isomerization zone working in the liquid phase and a second isomerization zone working in the gas phase. According to one or more embodiments, a first part of the raffinate 40 is sent to the liquid-phase isomerization unit, in order to obtain a first isomerate directly and at least partly feeding the separation unit 10 and a second part of the raffinate 40 is sent to the gas-phase isomerization unit, in order to obtain an isomerate which is sent to the xylene column 6.

According to one or more embodiments, the gas-phase isomerization zone is suitable for use under at least one of the following operating conditions:
- temperature of greater than 300° C., preferably from 350° C. to 480° C.;
- pressure of less than 4.0 MPa, and preferably from 0.5 to 2.0 MPa;
- hourly space velocity of less than 10 $h^{-1}$ (10 litres per litre per hour), preferably between 0.5 $h^{-1}$ and 6 $h^{-1}$;
- hydrogen to hydrocarbon mole ratio of less than 10, and preferably of between 3 and 6;
- in the presence of a catalyst including at least one zeolite having pores whose opening is defined by a ring containing 10 or 12 oxygen atoms (10 MR or 12 MR), and at least one group VIII metal in a content of between 0.1% and 0.3 by weight (reduced form), limits included.

According to one or more embodiments, the liquid-phase isomerization zone is suitable for use under at least one of the following operating conditions:
- temperature of less than 300° C., preferably 200° C. to 260° C.;
- pressure of less than 4 MPa, preferably 2 to 3 MPa;
- hourly space velocity (HSV) of less than 10 $h^{-1}$ (10 litres per litre per hour), preferably between 2 and 4 $h^{-1}$;

in the presence of a catalyst including at least one zeolite having channels, the opening of which is defined by a ring containing 10 or 12 oxygen atoms (10 MR or 12 MR), preferentially a catalyst including at least one zeolite having channels, the opening of which is defined by a ring containing 10 oxygen atoms (10 MR), and even more preferably a catalyst including a zeolite of ZSM-5 type.

The term HSV corresponds to the volume of hydrocarbon-based feedstock injected hourly, relative to the volume of catalyst charged.

According to one or more embodiments, the optional stabilization column 12 produces: at the bottom, a stabilized cut comprising (e.g. essentially) benzene and toluene 44, which is optionally recycled at the inlet of the feedstock separation unit 1 and/or of the unit for extraction of the aromatics 3; and, at the top, a cut of more volatile species 45 (e.g. C5−), which is removed from the aromatic complex.

According to one or more embodiments, the selective hydrogenolysis unit 9 is suitable for:
treating the monoaromatics containing between 9 and 10 carbon atoms 25; and
producing a hydrogenolysis effluent enriched in methyl-substituted aromatic compounds 46. Specifically, the selective hydrogenolysis unit 9 may be suitable for treating the aromatics containing between 9 and 10 carbon atoms 25 by converting one or more alkyl groups containing at least two carbon atoms (ethyl, propyl, butyl, isopropyl, etc. groups) attached to a benzene ring into one or more methyl groups, i.e. groups formed of a single $CH_3$ group. The major advantage of the selective hydrogenolysis unit 9 is that of increasing the content of $CH_3$ groups and lowering the content of ethyl, propyl, butyl, isopropyl, etc. groups in the feedstock of the isomerization unit 11, in order to increase the rate of production of xylenes, and notably of para-xylene, in said isomerization unit 11.

According to one or more embodiments, the selective hydrogenolysis unit 9 comprises at least one hydrogenolysis reactor suitable for use under at least one of the following operating conditions:
temperature of between 300° C. and 550° C., preferentially between 350° C. and 500° C. and even more preferentially between 370° C. and 450° C.;
pressure of between 0.1 and 3 MPa, preferentially between 0.2 and 2 MPa and more preferentially between 0.2 and 1 MPa;
$H_2$/HC (hydrocarbon-based feedstock) mole ratio of between 1 and 10 and preferentially between 1.5 and 6;
WHSV of between 0.1 and 50 $h^{-1}$ (e.g. 0.5-50 $h^{-1}$), preferentially between 0.5 and 30 $h^{-1}$ (e.g. 1-30 $h^{-1}$) and more preferentially between 1 and 20 $h^{-1}$ (e.g. 2-20 $h^{-1}$, 5-20 $h^{-1}$).

According to one or more embodiments, the hydrogenolysis reactor is operated in the presence of a catalyst including at least one metal from group VIII of the Periodic Table, preferably nickel and/or cobalt, deposited on a porous support comprising at least one crystalline or noncrystalline refractory oxide having structured or unstructured porosity. According to one or more embodiments, the group VIII metal is nickel. The presence of a promoter (group VIB, VIIB, VIII, IB or IIB) is also possible. The catalyst is supported on a refractory oxide (e.g. alumina or silica), optionally treated with a base in order to neutralize it.

According to one or more embodiments, the hydrogenolysis reactor is of fixed bed type and the catalyst support is in the form of extrudates. According to one or more embodiments, the hydrogenolysis reactor is of moving bed type, and the catalyst support is in the form of approximately spherical beads. A moving bed may be defined as being a gravity flow bed, such as those encountered in the catalytic reforming of gasolines.

According to one or more embodiments, the second hydrocarbon-based feedstock at 30 is a mixture of hydrocarbon-based compounds with a content of elemental oxygen at least greater than 1% by weight, preferentially 3% by weight, very preferentially 5% by weight, relative to the total weight of said feedstock. According to one or more embodiments, the second hydrocarbon-based feedstock 30 comprises or consists of lignocellulosic biomass or one or more constituents of lignocellulosic biomass chosen from the group formed by cellulose, hemicellulose and lignin.

Lignocellulosic biomass may consist of wood, agricultural waste or vegetable waste. Other non-limiting examples of lignocellulosic biomass material are farm residues (straw, corn stalks, etc.), forestry residues (products from first thinning), forestry products, dedicated crops (short rotation coppice), agrifood industry residues, organic household waste, waste from woodworking plants, waste construction wood, paper, whether or not recycled.

Lignocellulosic biomass may also come from byproducts of the papermaking industry such as Kraft lignin, or black liquor from the manufacture of paper pulp.

The lignocellulosic biomass may advantageously undergo at least one pretreatment step before it is introduced into the process according to the invention. Preferably, the biomass is ground and dried, until the desired particle size is obtained. A feedstock having a particle diameter of between 0.3 and 0.5 mm may advantageously be obtained. Typically, the size of the particles of the lignocellulosic biomass to be pyrolysed is a particle size sufficient to pass through a 1 mm screen up to a particle size sufficient to pass through a 30 mm screen.

According to one or more embodiments, when the second hydrocarbon-based feedstock 30 is solid (e.g. a feedstock of biomass type), the second hydrocarbon-based feedstock 30 to be pyrolysed is advantageously loaded into a pneumatic transportation or entrainment compartment so as to be entrained into a pyrolysis reactor with an entraining fluid. Preferably, the entraining fluid used is gaseous nitrogen. However, it is also envisaged that other non-oxidizing entraining fluids may be used. Preferably, a portion of the pyrolysis gas produced during the process may be recycled and used as entraining fluid. Said pyrolysis gas mainly consists of an uncondensable gaseous effluent, comprising at least carbon monoxide (CO) and carbon dioxide (CO2), and also advantageously comprising light olefins comprising from 2 to 4 carbon atoms. In this way, the cost of performing the pyrolysis may be reduced considerably. The second hydrocarbon-based feedstock 30 can be loaded into a feed hopper or another device which makes it possible to convey said feedstock into the entrainment compartment in an appropriate amount. In this way, a constant amount of feedstock is delivered to the entrainment compartment.

The entraining fluid advantageously transports the second hydrocarbon-based feedstock 30 from the entrainment compartment into the pyrolysis reactor through a feed tube.

Typically, the feed tube is cooled to maintain the temperature of the second hydrocarbon-based feedstock 30 at a required level before it enters the pyrolysis reactor. The feed tube can be cooled by jacketing the tube, typically with an air-cooled or liquid-cooled jacket. However, it is also envisaged for the feed tube not to be cooled.

According to one or more embodiments, the pyrolysis unit 13 comprises at least one pyrolysis reactor (e.g. a fluidized-bed reactor) suitable for use under at least one of the operating conditions listed below.

According to one or more embodiments, the pyrolysis step is performed at a temperature of between 400 and 1000° C., preferably between 400 and 650° C., preferably between 450 and 600° C. and preferably between 450 and 590° C. In particular, the use of hot regenerated catalyst obtained from a catalyst regeneration step may make it possible to provide temperature ranges for the reactor.

The pyrolysis step is also advantageously performed at an absolute pressure of between 0.1 and 0.5 MPa and at an HSV between 0.01 and 10 $h^{-1}$, preferably between 0.01 and 5 $h^{-1}$ and very preferably between 0.1 and 3 $h^{-1}$. The HSV is the ratio of the volume flow rate of feedstock to the volume of catalyst used.

According to one or more embodiments, the pyrolysis step is catalytic and is performed in the presence of a catalyst. Preferably, said step operates in the presence of a zeolite catalyst comprising and preferably consisting of at least one zeolite chosen from ZSM-5, ferrierite, zeolite beta, zeolite Y, mordenite, ZSM-23, ZSM-57, EU-1 and ZSM-11, and preferably the catalyst is a catalyst comprising only ZSM-5. The zeolite used in the catalyst employed in the catalytic pyrolysis step may advantageously be doped, preferably with a metal chosen from iron, gallium, zinc and lanthanum.

Under these conditions, the second hydrocarbon-based feedstock 30 will first undergo rapid pyrolysis in the reactor on coming into contact with the hot catalyst obtained from the regenerator, which performs the role of heat carrier in this step. The gases resulting from this pyrolysis will subsequently react on the catalyst, which this time performs its role as catalyst for catalysing the reactions producing the desired chemical intermediates.

In the pyrolysis unit 13, the second hydrocarbon-based feedstock 30 is notably converted, at least partially, into a pyrolysis effluent 31 comprising hydrocarbon-based compounds, the carbon number of which ranges from 6 to 10 carbon atoms, a pyrolysis gas 32 and byproducts 33. The pyrolysis effluent 31 feeds the first hydrocarbon-based feedstock 2 of the aromatic complex. The pyrolysis unit 13 also produces a pyrolysis gas 32 comprising CO, CO2 and H2, and byproducts 33.

The products obtained on conclusion of the pyrolysis step are advantageously recovered in the form of a gaseous effluent comprising BTXs.

Said gaseous effluent comprising the products obtained on conclusion of the pyrolysis step is then advantageously sent to a fractionation section, so as to separate at least the following cuts:

an uncondensable gas fraction, comprising at least carbon monoxide (CO) and carbon dioxide (CO2), a liquid cut known as BTX, comprising hydrocarbon-based compounds, the carbon number of which ranges from 6 to 10 carbon atoms, a liquid cut predominantly comprising compounds having a number of carbon atoms greater than 9, i.e. at least 50% by weight of C9+ compounds, and water.

Said uncondensable gas fraction may also advantageously comprise light olefins comprising from 2 to 4 carbon atoms.

The coked catalyst and the second unconverted hydrocarbon-based feedstock, usually known as "char", are advantageously withdrawn from the reactor and preferably sent to a stripper so as to remove the hydrocarbons potentially adsorbed, and thus prevent their combustion in the regenerator, by contacting with at least one gas chosen from steam, an inert gas, for instance nitrogen, and a portion of the uncondensable gas fraction resulting from fractionation of the gaseous effluent obtained from the pyrolysis step.

Said coked catalyst and the second unconverted hydrocarbon-based feedstock, which are optionally stripped, are advantageously sent to a regenerator where the coke and char are burnt off by adding air or oxygen, thus producing regenerated catalyst and a CO2-rich combustion gas.

According to one or more embodiments, the regenerated catalyst is advantageously recycled in the reactor of the pyrolysis step in order to undergo another cycle.

Advantageously, the pyrolysis step of the process according to the invention allows the production of at least 10% by weight and preferably at least 15% by weight of aromatics relative to the total mass of the reaction products obtained, with a selectivity of at least 65% and preferably of at least 70% of BTX.

The process thus comprises at least one pyrolysis step producing at least one BTX cut (pyrolysis effluent 31) and an uncondensable gas fraction (pyrolysis gas 32) comprising at least carbon monoxide and carbon dioxide.

The process also makes it possible to obtain, in addition to the BTX cut, a heavier liquid fraction, predominantly aromatic, called the "C9+ cut", which may advantageously be upgraded in a process external to the process according to the invention.

Preferably, at least a portion of the uncondensable gas fraction is recycled, preferably via a compressor, into the reactor of the pyrolysis step. This gas stream then serves as fluid for entraining the feed into said reactor. In this case, purging of said gaseous recycle effluent is preferably performed, preferably either upstream or downstream of said compressor.

According to one or more embodiments, the pyrolysis effluent 31 is a hydrocarbon cut predominantly containing (i.e. >50% by weight) molecules whose carbon number ranges from 6 to 10 carbon atoms. The pyrolysis effluent 31 may also contain molecules containing more than 10 carbon atoms and/or molecules containing 5 carbon atoms. The pyrolysis effluent 31 is rich in aromatics (e.g. >50% by weight) and preferably contains at least 20% by weight of benzene, preferentially at least 30% by weight, very preferably at least 40% by weight of benzene. According to one or more embodiments, the pyrolysis effluent 31 is treated to meet the required specifications of the first hydrocarbon-based feedstock 2 as described above, in order to have contents of sulfur-based, nitrogen-based and oxygen-based elements which are compatible with an aromatic complex.

According to one or more embodiments, the pyrolysis gas 32 comprises at least a portion of the uncondensable gas fraction and preferably comprises at least a portion of the CO2-rich combustion gas. According to one or more embodiments, the pyrolysis gas 32 produced by the pyrolysis unit 13 comprises a mixture predominantly containing (e.g. comprising at least 50% by weight) hydrogen, CO and CO2. According to one or more embodiments, the pyrolysis gas 32 comprises at least 20% by weight of CO, preferably at least 30% by weight of CO, very preferably at least 40% by weight of CO (e.g. at least 50% by weight of CO). According to one or more embodiments, the pyrolysis gas 32 comprises at least 0.2% by weight of H2, preferably at least 0.5% by weight of H2, very preferably at least 0.8% by weight of H2. According to one or more embodiments, the pyrolysis gas 32, at the outlet of the pyrolysis unit 13, contains at least 20% by weight of CO2. According to one or more embodiments, the pyrolysis gas 32, at the outlet of the pyrolysis unit 13, contains about 30% (e.g. ±10% by weight) by weight of CO2. According to one or more embodiments, the pyrolysis gas 32 contains methane, ethylene and propylene (e.g. less than 10% by weight) and also ethane, propane and water (e.g. less than 3% by weight).

According to one or more embodiments, the byproducts 33 comprise the C9+ fraction mainly consisting of more or less alkylated diaromatic and triaromatic compounds. This cut can be upgraded directly as bunker fuel, for example, or may undergo hydrotreating and/or hydrocracking in order to improve its properties and to be upgraded as jet fuel or as diesel oil.

According to one or more embodiments, a supply of H2 fed by the first supply line 34 is added to the pyrolysis gas 32 so that the H2/(CO2+CO) mole ratio of the pyrolysis gas 32 at the inlet of the WGS reaction section 50 is between 2 and 8, preferably between 2.5 and 6, very preferably between 2.5 and 4. The hydrogen supply may advantageously come from any process for producing hydrogen, for instance a steam reforming process or a catalytic reforming process, electrolysis of water, dehydrogenation of alkanes, and its hydrogen purity is usually between 75 vol % and 99.9 vol %.

According to one or more embodiments, an optional water supply fed by the second supply line 35 is added to the pyrolysis gas 32 so that the H2O/CO mole ratio is between 1 and 4, preferably between 1.5 and 2.5, very preferably between 1.8 and 2.2, such as 2 (±0.1). The recycling of the water produced in the CO2 aromatization section may prove to be sufficient, and not necessitate any additional supply of water.

In the WGS reaction section 50, the pyrolysis gas 32 optionally enriched with a supply of H2 and/or H2O is at least partially converted into a WGS gas 51 enriched in CO2 and in hydrogen (and thus depleted in CO and in H2O). Specifically, the WGS reaction corresponds to the reaction of CO and H2O to form CO2 and hydrogen.

The WGS reaction is well known to those skilled in the art (see, for example: Journal of Catalysis, vol. 229 (2005) pages 265-275; and Renewable and Sustainable Energy Reviews vol. 93 (2018) pages 549-565).

According to one or more embodiments, the WGS reaction section comprises at least one reactor used under at least one of the following operating conditions:
 temperature of between 250° C. and 450° C., preferentially between 300° C. and 500° C. and even more preferentially between 310° C. and 450° C.;
 pressure of between 0.1 and 5 MPa, preferentially between 0.2 and 4 MPa and more preferentially between 0.5 and 3 MPa;
 H2O/CO mole ratio of between 1 and 4, preferably between 1.5 and 2.5, very preferably between 1.8 and 2.2, such as 2 (±0.1);
 space velocity of the gas entering the reactor of between 1000 and 30 000 mL/$g_{cata}$/h.

According to one or more embodiments, the reactor of the WGS reaction section 50 is suitable for functioning as a fluid bed or as a fixed bed.

According to one or more embodiments, the WGS reaction is performed in the presence of a catalyst, such as a catalyst based on transition metals. For example, the catalyst may comprise iron and may optionally be promoted with chromium or copper. According to one or more embodiments, the catalyst comprises at least 50% by weight of Fe2O3, preferably at least 65% by weight of Fe2O3, relative to the total weight of the catalyst. According to one or more embodiments, the catalyst also comprises between 2% and 20% by weight of Cr2O3 and/or CuO, preferably between 5% and 15% by weight of Cr2O3 or CuO. According to one or more embodiments, the catalyst also comprises between 0.01% and 1% by weight of MgO, preferably between 0.1% and 0.5% by weight of MgO.

According to one or more embodiments, the WGS reaction section 50 is suitable for producing a WGS gas 51 comprising at least 50% by weight of CO2 in the mixture of CO, CO2 and H2, preferably at least 75% by weight of CO2, very preferably at least 80% by weight of CO2.

According to one or more embodiments, the pyrolysis gas 32 can be purified before being introduced into the WGS reaction section 50. Purification of the synthesis gas is directed towards removing the sulfur-based and nitrogen-based compounds, halogens, heavy metals and transition metals. The main technologies for the purification of synthesis gases are: adsorption, absorption, catalytic reactions.

The various purification methods are well known to a person skilled in the art: reference may be made, for example, to: Oil & Gas Science and Technology—Rev. IFP Energies Nouvelles, Vol. 68 (2013), No. 4, and to Applied Energy, Vol. 237 (2019), pages 227-240.

In accordance with the invention, the process comprises a step of conveying (preferably all of) the WGS gas 51 obtained from the WGS reaction section 50 into the CO2 aromatization reaction section 52.

According to one or more embodiments, the reaction section 52 for the aromatization of the CO2 comprises at least one reactor used under at least one of the following operating conditions:
 temperature of between 280° C. and 350° C., preferentially between 300° C. and 400° C. and even more preferentially between 320° C. and 380° C.;
 pressure of between 0.1 and 10 MPa, preferentially between 0.5 and 8 MPa and more preferentially between 2 and 4 MPa;
 space velocity of the gas entering the reactor of between 500 and 3000 mL/$g_{cata}$/h.

According to one or more embodiments, the reactor of the CO2 aromatization reaction section 52 is suitable for functioning as a fluid bed or as a fixed bed.

According to one or more embodiments, the aromatization reaction is performed in the presence of a catalyst, such as a catalyst comprising at least one transition metal and/or a porous support such as an alumina, a silica, an aluminosilicate or a zeolite. For example, the catalyst may comprise Cr2O3 and/or a zeolite, the outer surface of which may have been passivated by deposition of silica. According to one or more embodiments, the catalyst comprises a ZSM-5 zeolite which is optionally doped, for example doped with Zn. According to one or more embodiments, the catalyst comprises Cr2O3 mixed with Zn-ZSM-5@SiO2. @SiO2 means that the acidity of the outer surface of the ZSM-5 zeolite crystals has been neutralized by deposition of silica.

At the outlet of the CO2 aromatization reaction section 52, three streams may be separated:
 a hydrocarbon effluent 53 enriched in aromatic compounds, which is sent to the feedstock separation unit 1 as a mixture with the first hydrocarbon-based feedstock 2;
 optionally an effluent comprising the unconverted CO2, the CO formed and H2O, which is recycled via the optional recycling line 54 to the inlet of the WGS reaction section 50;
 optionally a water stream purged at the outlet of the aromatization reaction section 52.

Thus, the combination of a WGS reaction section 50, followed by a section 52 for the aromatization of the CO2 and of recycling of the unconverted CO2 and of the CO formed in the aromatization section, makes it possible to produce additional aromatics from the CO and CO2, which are byproducts of the pyrolysis unit 13.

The device and the process according to the invention thus make it possible to obtain gains of up to 480% by weight of aromatic compounds, in particular when the CO2 formed by combustion of the coke present on the pyrolysis catalyst is also treated.

In the present patent application, the groups of chemical elements are given, by default, according to the CAS classification (CRC Handbook of Chemistry and Physics, published by CRC Press, Editor-in-Chief D. R. Lide, 81st edition, 2000-2001). For example, group VIII according to the CAS classification corresponds to the metals from columns 8, 9 and 10 according to the new IUPAC classification; group VIb according to the CAS classification corresponds to the metals from column 6 according to the new IUPAC classification.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding application No. FR 2009872, filed Sep. 29, 2020 are incorporated by reference herein.

EXAMPLES

Example of Reference Device

Use is made of an example of a reference device for the transformation of a feedstock comprising a mixture of aromatic compounds resulting from a process for the conversion of lignocellulosic biomass based on a conversion by catalytic pyrolysis.

The reference device example is similar to the device represented in FIG. 1, except that the transalkylating unit 8 is replaced with a disproportionation unit. Furthermore, the reference device example does not employ the following units:
  heavy aromatics column 7;
  selective hydrogenolysis unit 9;
  stabilization column 12;
  WGS reaction section 50;
  aromatization reaction section 52.

The flow rates of said aromatic compounds of the feedstock to be treated, at the inlet of the reference device, are as follows:
  benzene: 2.63 t/h;
  toluene: 5.64 t/h;
  ethylbenzene: 0.15 t/h; and
  xylenes: 3.56 t/h.
i.e., a total of 11.98 t/h of aromatic compounds.

Furthermore, the pyrolysis reaction section produces CO and CO2, which are not converted into other chemical compounds. The flow rate of CO produced is 22.25 t/h and the flow rate of CO2 is 15.99 t/h. The combustion of the coke present on the pyrolysis catalyst produces 67 t/h of CO2, i.e. a total flow rate of CO2 not upgraded equal to 82.99 t/h.

In the reference device, all of the toluene is converted, by a disproportionation unit, into benzene and xylenes. The xylenes of the feedstock and those produced by disproportionation are isomerized to give para-xylene, which is separated from the xylenes mixture at thermodynamic equilibrium at the outlet of the isomerization unit, by means of a simulated moving bed adsorption unit. This set of unit operations makes it possible, in the best of cases (assuming a selectivity of 100% for each unit operation), to produce the following compounds:
  benzene: 5.02 t/h;
  para-xylene: 6.96 t/h
  aromatic total: 11.98 t/h.

Example of Device According to the Invention

The example of a device according to the invention makes it possible to increase the total amount of aromatics produced for the same flow rate of biomass feedstock entering the pyrolysis unit 13 as in the reference device, and in particular to increase the amount of para-xylene produced.

Relative to the reference device scheme, the WGS reaction section 50, the CO2 aromatization reaction section 51, and recycling of the unconverted CO2, of the CO formed and of the water formed at the outlet of the aromatization reaction section 52 to the inlet of the WGS reaction section 50 via line 54 are notably added. In this example, a supply of hydrogen is added via the first supply line 34 at the WGS inlet, and no supply of water is necessary. The water formed in the CO2 aromatization reaction is in a sufficient amount for the WGS reaction. Purging of the water produced via line 55 makes it possible to avoid accumulation of water in the process.

The pyrolysis gas 32, obtained from the catalytic pyrolysis unit 13, containing CO, CO2 as byproduct of the pyrolysis unit 13, the CO2 resulting from the combustion of the coke present on the pyrolysis catalyst and hydrogen is introduced into the WGS reaction section 50, with a supply of hydrogen via the first supply line 34. At the outlet of the WGS reaction section 50, the WGS gas 51 is introduced into a CO2 aromatization reaction section 52. At the outlet of the CO2 aromatization reaction section 52, the unconverted CO2, and the CO and H2O formed are recycled to the inlet of the WGS reaction section 50, and the water produced is purged via line 55. The hydrocarbon-based compounds produced in the aromatization section 52 are sent via line 53 to the inlet of the aromatic loop.

The conversion of the CO and CO2 by means of this process may be complete. The water formed may be advantageously used upstream of the pyrolysis unit 13 for the biomass pretreatment operations.

The overall material balances for the reference device and the device according to the invention are compared in Table 1.

TABLE 1

|  | Example of reference device | Example of device according to the invention |
|---|---|---|
| H2 supply (t/h) | 0 | 12.59 |
| Inlet of the aromatic complex (t/h) | | |
| C2-C4 paraffins | 0 | 4.28 |
| Benzene | 2.63 | 2.63 |

TABLE 1-continued

|  | Example of reference device | Example of device according to the invention |
|---|---|---|
| Toluene | 5.64 | 9.28 |
| Ethylbenzene | 0.15 | 0.15 |
| Xylenes | 3.56 | 22.26 |
| A9 aromatics | 0 | 9.34 |
| Products (t/h) |  |  |
| Benzene | 5.02 | 3.53 |
| p-Xylene | 6.96 | 40.13 |
| Total aromatics | 11.98 | 43.66 |
| C2-C4 paraffins | 0 | 4.28 |
| Water | 0 | 82.2 |
| CO | 22.25 | 0 |
| CO2 | 82.99 | 0 |
| H2 | 0.338 | 0 |

Table 1 shows that the implementation according to the invention makes it possible to produce 260% by weight more of aromatics (43.66 t/h instead of 11.98 t/h). This increase in aromatic compounds essentially concerns the para-xylene, which increases from 6.96 t/h to 40.13 t/h, i.e. a gain of 480%.

An amount of water equal to 82.2 t/h is also produced, and may be used in the biomass pretreatment steps upstream of the pyrolysis unit.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A process for converting a first hydrocarbon-based feedstock comprising aromatic compounds, comprising the following steps:
   fractionating the first hydrocarbon-based feedstock in a fractionation train in order to extract at least one cut comprising benzene, one cut comprising toluene and one cut comprising xylenes and ethylbenzene;
   separating the cut comprising xylenes and ethylbenzene in a xylenes separating unit and producing an extract comprising para-xylene and a raffinate comprising ortho-xylene, meta-xylene and ethylbenzene;
   isomerizing the raffinate in an isomerization unit and producing an isomerate enriched in para-xylene;
   sending the isomerate enriched in para-xylene to the fractionation train;
   treating a second hydrocarbon-based feedstock in a pyrolysis unit to produce at least one pyrolysis effluent comprising hydrocarbon-based compounds containing from 6 to 10 carbon atoms, feeding, at least partially, the first hydrocarbon-based feedstock and to produce a pyrolysis gas comprising at least CO, CO2 and H2;
   treating the pyrolysis gas in a WGS water gas shift reaction section to produce a WGS gas enriched in CO2 and in hydrogen;
   at least partly treating the WGS gas enriched in CO2 and in hydrogen in an aromatization reaction section to produce a hydrocarbon effluent comprising aromatic compounds; and
   feeding the first hydrocarbon-based feedstock with the hydrocarbon effluent (53).

2. The conversion process according to claim 1, further comprising recycling, to the inlet of the WGS reaction section, the unconverted CO2 and also the CO and water formed during the aromatization reaction.

3. The conversion process according to claim 1, further comprising providing a supply of H2 and/or H2O in the pyrolysis gas by at least one supply line.

4. The conversion process according to claim 1, in which the pyrolysis unit comprises at least one reactor used under at least one of the following operating conditions:
   an absolute pressure of between 0.1 and 0.5 MPa and an HSV of between 0.01 and 10 h$^{-1}$, the HSV being the ratio of the flow rate by volume of feedstock to the volume of catalyst used;
   a temperature of between 400° C. and 1000° C.;
   a zeolite catalyst comprising at least one zeolite selected from the group consisting of ZSM-5, ferrierite, zeolite beta, zeolite Y, mordenite, ZSM-23, ZSM-57, EU-1 and ZSM-11.

5. The conversion process according to claim 1, in which the WGS reaction section comprises at least one reactor used under at least one of the following operating conditions:
   temperature of between 250° C. and 450° C.;
   pressure of between 0.1 and 5 MPa;
   an H2O/CO mole ratio of between 1 and 4;
   space velocity of the gas entering the reactor of between 1000 and 30 000 mL/g$_{cata}$/h.

6. The conversion process according to claim 1, in which the reaction section for the aromatization of the CO2 comprises at least one reactor used under at least one of the following operating conditions:
   temperature of between 280° C. and 350° C.;
   pressure of between 0.1 and 10 MPa;
   space velocity of the gas entering the reactor of between 500 and 3000 mL/g$_{cata}$/h.

7. The conversion process according to claim 1, in which the isomerization unit comprises a gas-phase isomerization zone and/or a liquid-phase isomerization zone,
   in which the gas-phase isomerization zone is used under at least one of the following operating conditions:
   temperature of greater than 300° C.;
   pressure of less than 4.0 MPa;
   hourly space velocity of less than 10 h$^{-1}$;
   hydrogen to hydrocarbon mole ratio of less than 10;
   in the presence of a catalyst including at least one zeolite having channels whose opening is defined by a ring containing 10 or 12 oxygen atoms, and at least one group VIII metal in a content of between 0.1% and 0.3% by weight, limits included, and
   in which the liquid-phase isomerization zone is used under at least one of the following operating conditions:
   temperature of less than 300° C.;
   pressure of less than 4 MPa;
   hourly space velocity of less than 10 h$^{-1}$;
   in the presence of a catalyst including at least one zeolite having channels whose opening is defined by a ring containing 10 or 12 oxygen atoms.

8. The conversion process according to claim 1, in which the catalyst is a catalyst is ZSM-5 only.

9. The conversion process according to claim 1, in which the pyrolysis unit comprises at least one reactor used under at least one of the following operating conditions:

an absolute pressure of between 0.1 and 0.5 MPa and an HSV of between 0.1 and 3 h$^{-1}$, the HSV being the ratio of the flow rate by volume of feedstock to the volume of catalyst used;

a temperature of between 450° C. and 590° C.

10. The conversion process according to claim 1, in which the WGS reaction section comprises at least one reactor used under at least one of the following operating conditions:

temperature of between 310° C. and 450° C.;
pressure of between 0.5 and 3 MPa;
an H2O/CO mole ratio of between 1.8 and 2.2;
space velocity of the gas entering the reactor of between 1000 and 30 000 mL/g$_{cata}$/h.

11. The conversion process according to claim 1, in which the reaction section for the aromatization of the CO2 comprises at least one reactor used under at least one of the following operating conditions:

temperature of between 300° C. and 400° C.;
pressure of between 2 and 4 MPa;
space velocity of the gas entering the reactor of between 500 and 3000 mL/g$_{cata}$/h.

12. The conversion process according to claim 1, in which the reaction section for the aromatization of the CO2 comprises at least one reactor used under at least one of the following operating conditions:

temperature of between 320° C. and 380° C.;
pressure of between 2 and 4 MPa;
space velocity of the gas entering the reactor of between 500 and 3000 mL/g$_{cata}$/h.

13. The conversion process according to claim 1, which is performed in a device for the conversion of a first hydrocarbon-based feedstock comprising aromatic compounds, said device comprising:

a fractionation train suitable for extracting at least one cut comprising benzene, one cut comprising toluene and one cut comprising xylenes and ethylbenzene from the first hydrocarbon-based feedstock;

a xylenes separating unit suitable for treating the cut comprising xylenes and ethylbenzene and for producing an extract comprising para-xylene and a raffinate comprising ortho-xylene, meta-xylene and ethylbenzene;

an isomerization unit suitable for treating the raffinate and for producing an isomerate enriched in para-xylene, which is sent to the fractionation train;

a pyrolysis unit suitable for treating a second hydrocarbon-based feedstock, for producing at least one pyrolysis effluent comprising hydrocarbon-based compounds of 6 to 10 carbon atoms at least partially feeding the hydrocarbon-based feedstock, and for producing a pyrolysis gas comprising at least CO, CO2 and H2;

a WGS water gas shift reaction section suitable for treating the pyrolysis gas and for producing a WGS gas enriched in CO2 and in hydrogen;

a CO2 aromatization reaction section suitable for:
at least partly treating the WGS gas to produce a hydrocarbon effluent (53) comprising aromatic compounds, and
feeding the first hydrocarbon-based feedstock with the hydrocarbon effluent.

14. The process according to claim 13, wherein the device further comprises a recycling line suitable for recycling, to the inlet of the WGS reaction section, the unconverted CO2 and also the CO and water formed during the aromatization reaction.

15. The process according to claim 13, wherein the device further comprises at least one supply line to provide a supply of H2O and/or hydrogen in the pyrolysis gas, upstream of the WGS section.

16. The process according to claim 13, wherein in the device, the fractionation train is suitable for extracting a C9-C10 monoaromatics cut from the first hydrocarbon-based feedstock.

17. The process according to claim 16, wherein the device further comprises a transalkylation unit suitable for treating the C9-C10 monoaromatics cut with the cut comprising toluene and for producing xylenes which are sent to the fractionation train.

18. The process according to claim 17, wherein the device further comprises a selective hydrogenolysis unit suitable for:
treating the C9-C10 monoaromatics cut; and
producing a hydrogenolysis effluent enriched in methyl-substituted aromatic compounds which is sent to the transalkylation unit.

19. The process according to claim 13, wherein the device further comprises a disproportionating unit suitable for at least partly treating the cut comprising toluene and for producing a xylene-enriched cut, which is recycled to the isomerization unit.

* * * * *